United States Patent
Beekman et al.

(10) Patent No.: US 10,328,285 B2
(45) Date of Patent: Jun. 25, 2019

(54) HADRON RADIATION INSTALLATION AND VERIFICATION METHOD

(71) Applicant: Technische Universiteit Delft, Delft (NL)

(72) Inventors: Frederik Johannes Beekman, Ultrecht (NL); Victor Robert Bom, Delft (NL)

(73) Assignee: Technische Universiteit Delft, Delft (NL)

( * ) Notice: Subject to any disclaimer, the term of this patent is extended or adjusted under 35 U.S.C. 154(b) by 0 days.

(21) Appl. No.: 15/623,587

(22) Filed: Jun. 15, 2017

(65) Prior Publication Data
US 2017/0281977 A1 Oct. 5, 2017

Related U.S. Application Data

(62) Division of application No. 14/351,391, filed as application No. PCT/NL2012/050719 on Oct. 12, 2012, now Pat. No. 9,707,411.

(51) Int. Cl.
*G01T 1/29* (2006.01)
*A61N 5/10* (2006.01)

(52) U.S. Cl.
CPC ......... *A61N 5/1067* (2013.01); *A61N 5/1043* (2013.01); *A61N 5/1048* (2013.01);
(Continued)

(58) Field of Classification Search
CPC ....... G01T 1/24; G01T 1/2018; G01T 1/2928; H04N 5/32; H01L 27/14676
See application file for complete search history.

(56) References Cited

U.S. PATENT DOCUMENTS

| 4,870,287 A | 9/1989 | Cole et al. |
| 6,814,694 B1 | 11/2004 | Pedroni |

(Continued)

FOREIGN PATENT DOCUMENTS

| EP | 0779081 A2 | 6/1997 |
| FR | 2930995 A1 | 11/2009 |

(Continued)

OTHER PUBLICATIONS

Machine translation of FR2930995 A1.
(Continued)

*Primary Examiner* — David P Porta
*Assistant Examiner* — Mamadou Faye
(74) *Attorney, Agent, or Firm* — Hoffman & Baron, LLP

(57) ABSTRACT

A hadron radiation installation adapted to subject a target to irradiation by a hadron radiation beam includes a target support configured to support, preferably immobilize, a target; a hadron radiation apparatus adapted to emit a hadron radiation beam along a beam axis to irradiate the target supported by the target support, the radiation beam penetrating into the target. The radiation apparatus has a control system at least comprising a beam penetration depth control allowing at least to control and vary the penetration depth of the radiation beam into the target. The installation has a radiation beam range sensor device adapted to determine the penetration depth of said radiation beam into the target, where the range sensor device includes a gamma camera responsive to prompt gamma rays that are emitted while the hadron radiation beam penetrates into the target.

4 Claims, 8 Drawing Sheets

(52) U.S. Cl.
CPC ......... *A61N 5/1071* (2013.01); *A61N 5/1075* (2013.01); *A61N 5/1084* (2013.01); *G01T 1/2935* (2013.01); *A61N 2005/1052* (2013.01); *A61N 2005/1076* (2013.01); *A61N 2005/1087* (2013.01)

(56) References Cited

U.S. PATENT DOCUMENTS

| | | | |
|---|---|---|---|
| 8,017,906 B2* | 9/2011 | Nelson | G01T 1/2018 250/252.1 |
| 8,481,951 B2* | 7/2013 | Jongen | A61N 5/1048 250/363.05 |
| 8,983,024 B2 | 3/2015 | Zhang et al. | |
| 9,358,406 B2* | 6/2016 | Prieels | A61N 5/1048 |
| 2003/0036700 A1 | 2/2003 | Weinberg | |
| 2008/0078937 A1 | 4/2008 | Tsuchiya et al. | |
| 2008/0237476 A1 | 10/2008 | Uribe et al. | |
| 2011/0057110 A1 | 3/2011 | Testa et al. | |
| 2012/0153176 A1 | 6/2012 | Tsukerman | |
| 2014/0061493 A1 | 3/2014 | Priells et al. | |

FOREIGN PATENT DOCUMENTS

| | | |
|---|---|---|
| WO | 99/42035 A1 | 8/1999 |
| WO | 2010/000857 A1 | 1/2010 |

OTHER PUBLICATIONS

Busca, P. et al., "Development of a camera for imaging of prompt gamma rays in measurements of proton beam range," PSD9, Aberystwyth, UK, Sep. 15, 2011.

Fiorini, Prof. Carlo, "Laboratory of Radiation Detectors and X and ν-ray Instrumentation," XP-002680941, 2007596.

Polf, J.C., et al., "Measurement and calculation of characteristic prompt gamma ray spectra emitted during proton irradiation," Phys. Med. Biol. 54 (2009) N519-N527.

Min, Chul, et al., "Development of an Array-Type Prompt Gamma Detection System for the Online Measurement of the Range of the Proton Beam in a Patient: a Monte Carlo Feasibility Study," Journal of the Korean Physical Society, vol. 52, No. 3, Mar. 2008, pp. 888-891.

Min, Chul, et al., "Prompt gamma measurements for locating the dose falloff region in the proton therapy," Applied Physics Letters 89, 183517 (2006).

International Search Report for priority PCT application, dated Mar. 26, 2013.

International Preliminary Report on Patentability for priority PCT application, dated Apr. 15, 2014.

* cited by examiner

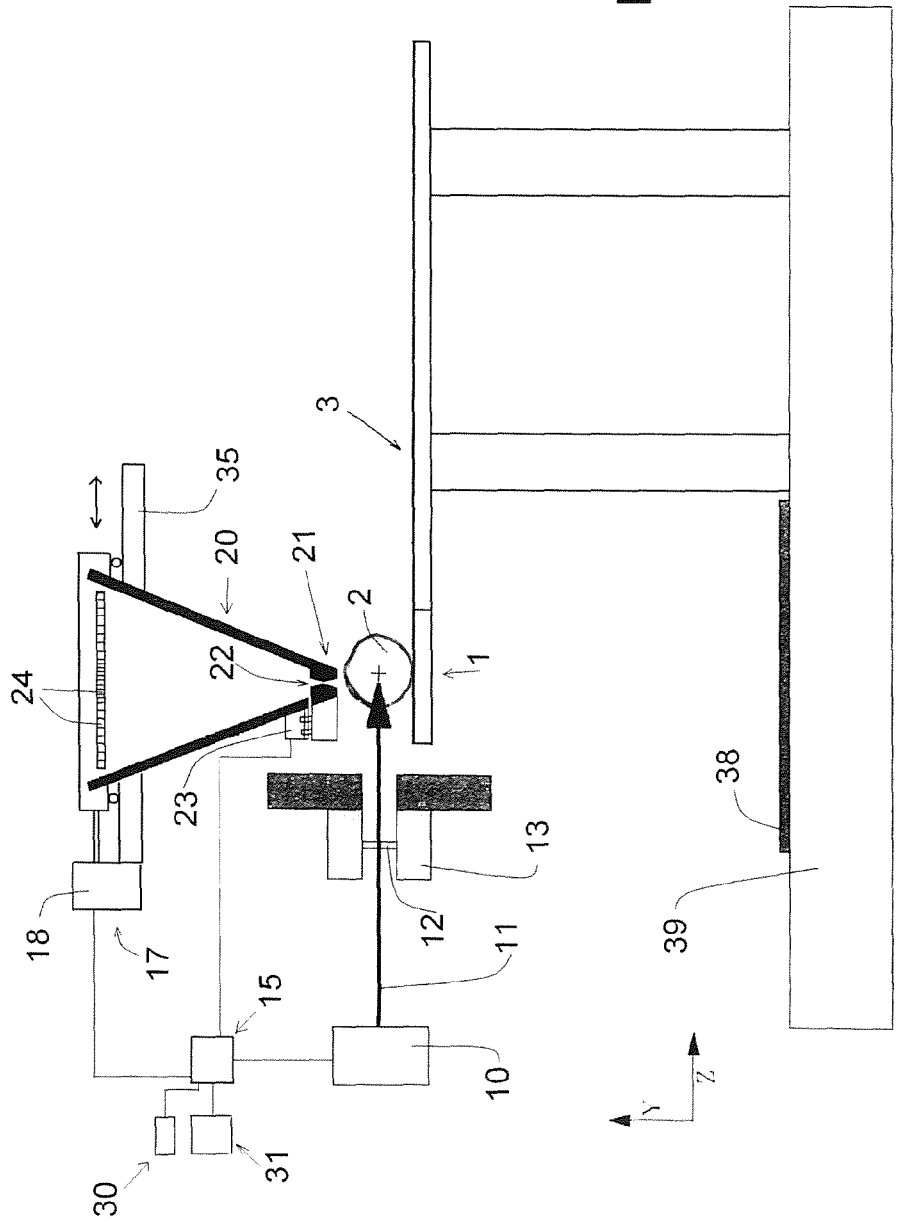

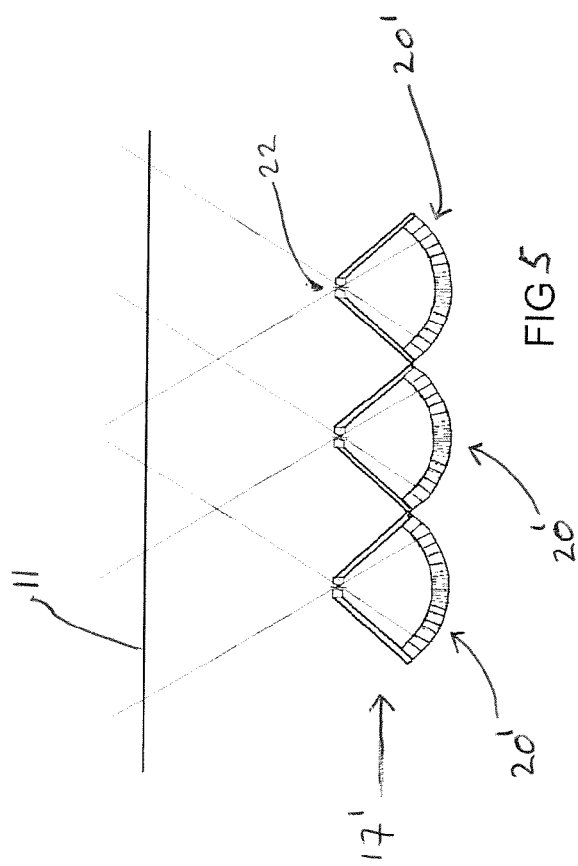

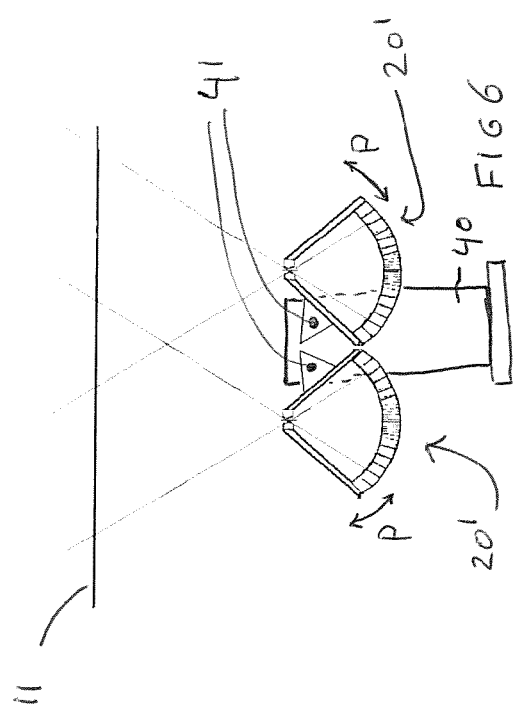

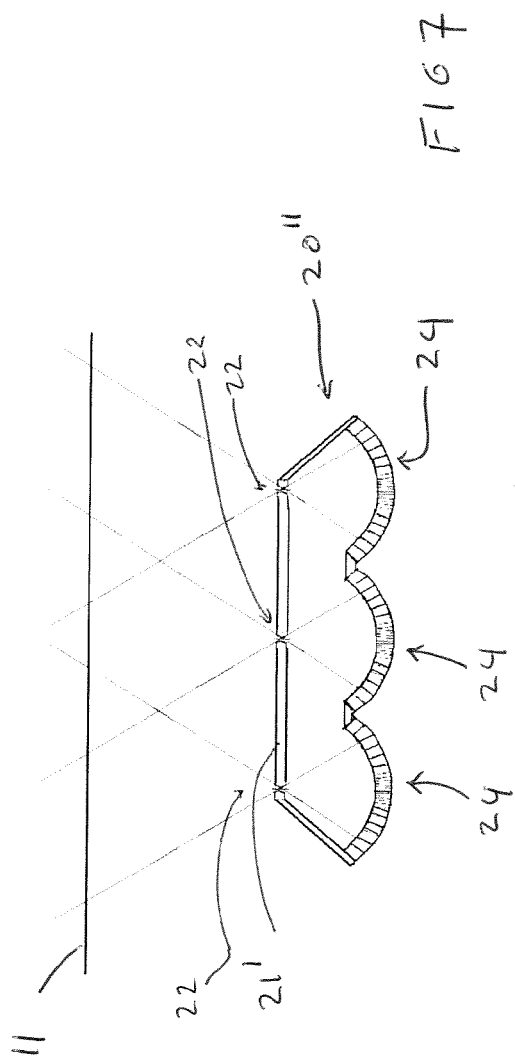

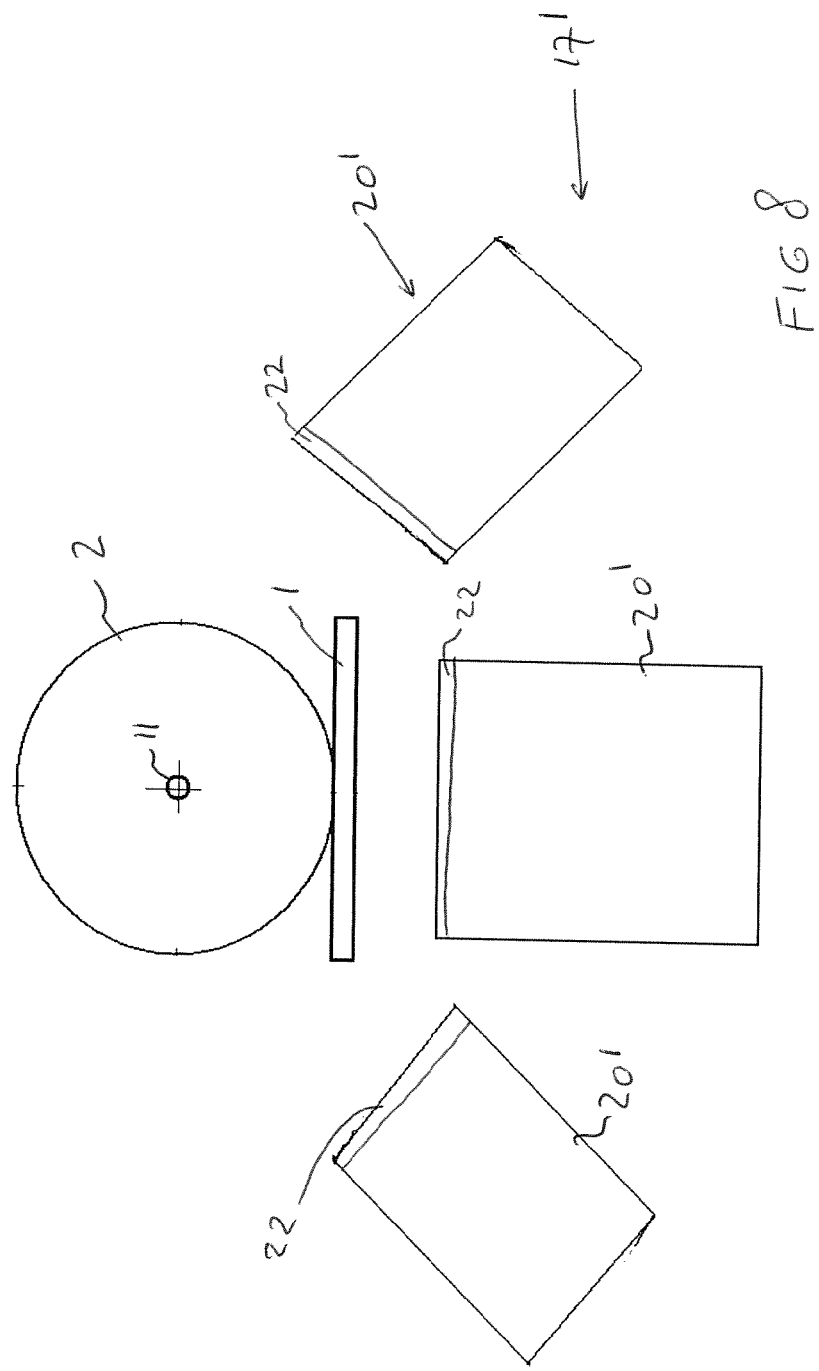

HADRON RADIATION INSTALLATION AND VERIFICATION METHOD

CROSS-REFERENCE TO RELATED APPLICATIONS

This application is a continuation of U.S. patent application Ser. No. 14/351,391, filed Apr. 11, 2014, which is the National Stage of International Application No. PCT/NL2012/050719 filed Oct. 12, 2012, which claims the benefit of Netherlands Application No. 2007596, filed Oct. 14, 2011, the contents of which are incorporated by reference herein.

FIELD OF THE INVENTION

The present invention relates to the field of hadron radiation therapy.

BACKGROUND OF THE INVENTION

In the field of radiation therapy, e.g. for the treatment of tumors, it is understood that hadron radiation therapy (notably with protons or ions, such as carbon-ion therapy) offers significant advantages over X-ray or gamma ray therapies. In general hadron radiation therapy is an upcoming cancer treatment in which a hadron beam is used for irradiation. The number of hadron radiation therapy centers, mainly equipped with a proton radiation therapy installation, is growing rapidly and world wide over 50000 patients have been treated up to now.

The dominant processes by which protons and other hadrons deposit energy in tissue are atomic ionization and excitation. Most of the kinetic energy is deposited in the Bragg Peak (BP) at the very end of the track. Hadron radiation therapy has the potential to realize an attractive dose conformation, thus sparing the healthy tissue surrounding the tumor. This allows for either dose escalation for hypoxic tumors or for fewer side effects for nearby organs at risk. These are major advantages in the treatment of tumors located in critical parts of the body, such as the brain, e.g. near the eye.

Many recently commissioned hadron radiation therapy systems use the spot scanning technique wherein magnetic fields are used to steer the radiation beam in the desired direction. A pencil beam is stepped or scanned many times over the tumor or other defined treatment field of the target, with the energy and intensity being varied so that the dose in each microvolume of the tumor can be optimized. The beam intensity is continuously controlled. Not the entire tumor is irradiated at the same time but the irradiation is done spot after spot and slice after slice.

It is known to carefully plan a radiation session by making CT images of the patient, making calculations (often based on earlier phantom testing), etc. However, the actual position of the Bragg Peak within the actual patient depends among others on the characteristics of intermediate tissues, that may differ with the patient and with the irradiation position. Also anatomical differences may occur in the time span between planning and actual performance of the therapeutic radiation session, for example local changes of the patient anatomy, tissue composition, etc. It is therefore common understanding that deviations are present between the treatment plan and the actually applied radiation therapy. In particular with regard to the penetration depth of the beam into a human brain the actual position of the Bragg Peak is observed to deviate significant, e.g. between 10 and 15 millimeters, from the planned position. Critical tissues located near the tumor to be treated could receive an overdose, or the tumor may receive an underdose as a result.

It is therefore of great importance to verify the Bragg Peak position, preferably even during the hadron radiation therapy session, to be sure that the dose is delivered as planned.

Positron Emission Tomography (PET) is currently the only method effectively used in this field for dose verification. Isotopes that decay by positron emission are formed by nuclear reactions in the proton track and can be used for PET imaging, allowing to check the administered dose profile. However, the half-life of the suited isotopes is of the order the duration of the fraction or longer. Dose profile monitoring with PET within the time duration of a spot-step, commonly less than 0.1 s, therefore seems unlikely.

Research is currently also conducted into the use of prompt gamma rays for hadron beam penetration verification, monitoring, and possibly also for real-time control of the beam during irradiation of the target. Nuclear fragmentation reactions occur along the track in the target resulting in the emission of large numbers of neutrons and prompt gamma rays. These gamma rays arise from the statistical decay of nuclei exited at energies below the nuclear binding energy (8 MeV). Prompt gamma rays are a likely candidate for dose monitoring because their number is much larger than the number of PET isotopes. The absence of washout effects as seen with PET and the close correlation between the beam penetration depth range and the prompt gamma ray production position are important additional advantages. The correlation mentioned is the result of the fact that nuclear reactions occur up to the last few millimeters of the track where the hadrons energy falls below the Coulomb barrier threshold.

In WO2010/000857 several approaches of the use of prompt gamma rays are discussed, mainly aimed to work towards a real-time measurement of the spatial dose distribution in the target.

In one embodiment an Anger gamma camera is proposed wherein a collimator is placed directly over a flat panel detection crystal and a PMT array at the rear of the detection crystal. The collimator consists of a thick sheet of gamma ray blocking material, e.g. lead, with a multitude of adjacent holes through it. The camera is installed to have its optical axis at right angles to the beam axis. The PMT may be arranged in a two-dimensional array and it is envisaged that with the use of two such camera's a three dimensional image of the distribution of prompt gamma rays can be obtained.

In another embodiment WO2010/00857 proposes a pinhole gamma camera, wherein a single pinhole collimator is arranged at a distance in front of a single scintillation element type detector. The pinhole is configured and arranged so as to provide a field of view of the camera that encompasses the entire track of the proton beam within the target, so that there is no need to move the camera to observe the prompt gamma distribution along the track. Depending on whether a linear or two-dimensional array of PMTs is used, a one dimensional or two dimensional image of the prompt gamma distribution is obtained.

The present inventors consider the Anger camera and single pinhole gamma camera as proposed in WO2010/00857 unsuited as the collimator attenuates most of the incident gamma photons and thus greatly limits the sensitivity of the camera. The potential for real-time measurement of proton beam penetration depth is therefore severely restricted.

In a recent proposal it has been suggested to use in a hadron radiation installation a gamma camera with a slit collimator having an elongated slit aperture that is arranged substantially at right angles to the beam axis and with a 2D-detector. This detector has a single scintillation element embodied as a flat panel detection crystal and a 2D-array of photodetectors at the rear side of the crystal. The slit is configured as a knife-edge type slit with a fixed width. The collimator and slit thereof are arranged such with respect to the target that the camera has a field of view that encompasses the entire track of the beam within the target, so that there is no need to move the camera to observe the prompt gamma distribution along the track. As the slit aperture is greater in cross-section than the single pinhole and also provides less attenuation than the collimator in the Anger camera, the above-mentioned problems are potentially solvable.

OBJECT OF THE INVENTION

It is an object of the present invention to propose further improvements to a proton radiation therapy installation with prompt gamma based sensor.

It is a further object of the present invention to provide a proton radiation therapy installation with prompt gamma based sensor that allows for real-time monitoring and preferably real-time control of the proton beam penetration into the target during the radiation session.

SUMMARY OF THE INVENTION

According to a first aspect thereof the present invention provides an installation which is characterized in that the collimator is a variable width slit collimator having an elongated slit aperture of variable width, said collimator having a first collimator member and a second collimator member that each define one of the opposed longitudinal edges of the aperture, said collimator having a slit width actuator mechanism for displacing and positioning said collimator members relative to one another.

By allowing for variation of the slit width the utility of the installation is significantly increased, notably when in a suitable design the slit width can be varied in the course of a radiation session, e.g. to optimize the functioning of the radiation beam range sensor device and/or to enhance or optimize one or more of the resolution, accuracy, quality, and reliability of the gamma camera.

The target can for example be a human body, e.g. the head for treatment of a brain tumor, an animal body, e.g. for research purposes, or a phantom, e.g. a water phantom. As is known a phantom is commonly used for verification procedures, including such verification in the course of planning a radiation session to be performed on a human or animal body.

In a preferred embodiment the radiation apparatus is adapted to emit a pencil radiation beam.

In a preferred embodiment the hadron radiation therapy systems is adapted to perform the spot scanning technique wherein magnetic fields of a magnet assembly are used to steer the radiation beam in a desired direction. The pencil beam is stepped or scanned in a session many times over a tumor or other defined treatment field, with the energy and intensity being varied so that the dose in each microvolume of the tumor can be optimized. The beam intensity is continuously controllable during the session.

In an embodiment the radiation beam range sensor device is linked to a monitoring system of the proton radiation apparatus to provide at least beam penetration depth information, preferably during a radiation session. This e.g. allows the operator to verify actual penetration depth during a verification session or therapy session.

In a preferred embodiment the radiation beam range sensor device is linked to said beam penetration depth control of said control system to provide at least beam penetration depth feedback information to said beam penetration depth control.

In a preferred embodiment the collimator is supported such that the slit aperture extends substantially perpendicular to the beam axis, and the detector comprises an array of multiple elongated scintillation elements in parallel and side-by-side arrangement, each scintillation element having a length along a longitudinal axis that is parallel to the collimator slit aperture, a width perpendicular to said length and parallel to an incident face of said scintillation element, and a height perpendicular to said length and perpendicular to an incident face of said scintillation element, wherein said length is greater than each of said width and said height.

It is noted that the above preferred embodiment also relates to a second aspect of the invention. This aspect concerns a hadron radiation installation adapted to subject a target to irradiation by a hadron radiation beam, said installation comprising:

a target support configured to support a target;

a hadron radiation apparatus adapted to emit a hadron radiation beam along a beam axis to irradiate the target supported by the target support, said radiation beam penetrating into the target, wherein the radiation apparatus has a control system at least comprising a beam penetration depth control allowing at least to control and vary the penetration depth of the radiation beam into the target, a radiation beam range sensor device adapted to determine the penetration depth of said radiation beam into the target, wherein said range sensor device comprises a gamma camera responsive to prompt gamma rays that are emitted while said radiation beam penetrates into the target, said gamma camera comprising:

a collimator having a wall that blocks gamma radiation and an aperture in said wall, a detector comprising one or more scintillation elements upon which gamma radiation passing through said aperture of the collimator is incident, an electronic readout mechanism associated with said detector, wherein the collimator of the gamma camera is a slit collimator having an elongated slit aperture, characterized in that the detector comprises an array of multiple elongated scintillation elements in parallel and side-by-side arrangement, each scintillation element having a length along a longitudinal axis that is parallel to the collimator slit aperture, a width perpendicular to said length and parallel to an incident face of said scintillation element, and a height perpendicular to said length and perpendicular to an incident face of said scintillation element, wherein said length is greater than each of said width and said height.

In this second aspect of the invention it is envisaged that the slit collimator preferably has a variable slit width as in the first aspect of the invention, however, that improvements over the prior art approaches can also be reached when the collimator has a fixed slit width, so in absence of any slit width actuator mechanism.

In particular this second aspect of the invention aims to provide measures that allows for an enhanced accuracy and speed of the gamma camera, mainly aimed to make a real-time feedback to the penetration depth control possible during a radiation session. As explained in the introduction presently proposed gamma cameras are unsuited or hardly suited to achieve this goal.

By providing elongated scintillation elements parallel to the collimator slit, which is substantially perpendicular to the beam axis, each scintillation element establishes as it were a mono-directional cross-section of the distribution of prompt gamma rays that are emitted. When combined with a suitable geometrical magnification factor due to the relative distance of the detector to the collimator slit compared to the distance between the radiation beam and the collimator slit, the combination of different cross-sections allows for an accurate determination of the penetration depth of the radiation beam into the target.

In an embodiment the detector contains a single array of such scintillation elements, preferably the length of the scintillation elements corresponding at least to the length of the slit of the collimator.

In an embodiment the scintillation elements each are embodied as an elongated strip of solid scintillation material, each strip having an incident face, a rear face opposite the incident face, side faces, and end faces at longitudinal ends of the strip, wherein a photodetector is connected to an end face of the strip, e.g. directly or via a light guide, e.g. via a light guide fibre. In an embodiment each strip is connected to at only one end face to a photodetector, however it is also possible that a respective photodetector is connected to each end face of the strip.

It is preferred to embody the photodetectors—when present—as silicon photomultipliers (SiPMs).

In an embodiment the scintillating material is BGO (Bismuth germanate) or LYSO ($Lu_{1.8}Y_{0.2}SiO_5(Ce)$). In another embodiment a scintillation element is composed of a suitable scintillation liquid held in a longitudinal container. For example the liquid is held in a glass or other transparent material container. For example one or more photodetectors are arranged at a longitudinal end or ends of the container.

It is noted that the invention also envisages the use of direct-conversion detectors that directly convert gamma rays into an electric charge.

In a possible embodiment of the detector the scintillation elements in a central group of scintillation elements of an array each have a smaller width than the width of individual scintillation elements in end groups of scintillation elements between which end groups said central group is located. This basically allows for a greater resolution of the gamma camera with respect to prompt gamma rays that are incident on the central group compared to the end groups of scintillation elements. In particular in view of determination of the actual position of the Bragg Peak this may be used advantageously.

In an embodiment the radiation beam range sensor device is adapted to control the slit width actuator mechanism in dependency of the actual gamma count rate. In a possible version thereof the radiation beam range sensor device is adapted to control the slit width actuator mechanism so as to increase the slit width if the actual gamma count rate is below a predetermined lower threshold, and to decrease the slit width if the actual gamma count rate is above a predetermined upper threshold, said upper threshold representing a higher count rate than the lower threshold. This allows e.g. to obtain a reliable result of the gamma camera, e.g. enhancing the accuracy/reliability of the beam penetration depth control if the gamma camera output is used as feedback signal.

In an embodiment control system of the apparatus is adapted to input and store (or actually stores) in a memory one or more sets of radiation session control data corresponding to one or more radiation sessions to be performed with the radiation beam apparatus, wherein the slit width actuator mechanism of the collimator is linked to the control system, and wherein said radiation session control data includes data representing one or more planned beam penetration depths of a radiation session to be performed, e.g. a planned pattern of varying beam penetration depth, and wherein said radiation session control data includes data representing one or more planned slit widths of the collimator for a radiation session to be performed, e.g. a planned pattern of variation of the slit width of the collimator to be performed in synchronicity with the varying beam penetration depth pattern. This embodiment allows to set or adjust during a session the slit width in order to obtain optimal and/or reliable results of the gamma camera. The planned slit widths of the collimator for a radiation session to be performed can be obtained by suitable calculation and/or by performing a verification session on a suitable phantom.

In an embodiment the radiation apparatus is adapted to vary the position and/or angular orientation of the beam axis relative to the target support and to vary the penetration depth into the target so as to locate the Bragg Peak of the emitted pencil type proton radiation beam at a planned location at least represented by X,Y,Z coordinates, wherein the Z-coordinate is along the beam axis and the X and Y coordinates are along orthogonal axes in a plane perpendicular to the beam axis.

In an embodiment the control system is adapted to input and store in a memory one or more sets of radiation session control data corresponding to one or more radiation sessions to be performed with the radiation beam apparatus, wherein said radiation session control data includes data representing a planned pattern of X-Y motion of the pencil type radiation beam for a radiation session to be performed, and wherein said radiation session control data includes data representing a pattern of variation of the slit width of the collimator in synchronicity with the planned pattern of X-Y motion of the radiation beam for radiation session to be performed.

If the beam axis is at different distances with respect to the collimator during a session, this may well influence the "capturing" of prompt gamma rays by the gamma camera and therefore the output signal of the gamma camera.

In an embodiment it is therefore proposed that the gamma camera is movably supported by a gamma camera support structure so as to be movable in a Y-axis direction that is substantially perpendicular to the beam axis without moving the target support relative to the beam apparatus, and wherein a Y-as drive is provided to controllably move the gamma camera in said Y-axis direction.

This embodiment e.g. allows to compensate for motion of the beam axis during the session relative to the collimator.

In an embodiment the control system is adapted to input and store in a memory one or more sets of radiation session control data corresponding to one or more radiation sessions to be performed with the radiation beam apparatus, wherein said radiation session control data includes data representing a pattern of motion of the radiation beam for a radiation session to be performed, and wherein said radiation session control data includes data representing a desired slit width of the slit aperture of the collimator, which width is to be maintained in combination with the planned pattern of motion of the radiation beam throughout a radiation session to be performed.

In an embodiment the collimator, preferably the gamma camera including the collimator, is movably supported so as to be movable, e.g. with the slit aperture substantially perpendicular to the beam axis, in a Z-axis direction substantially parallel to the beam axis without moving the target support relative to said proton beam apparatus, preferably over a length of at least 20 centimeters, e.g. when the installation is designed for radiation tumors in the head of a human patient.

In an embodiment a Z-axis drive is provided to controllable move the collimator, preferably the gamma camera including the collimator, in Z-axis direction.

This embodiment is in particular useful in a detector design wherein the scintillation elements in a central group of scintillation elements of an array each have a smaller width than the width of individual scintillation elements in end groups of scintillation elements between which end groups said central group is located.

An advantage of Z- axis motion of the collimator or entire gamma camera may be that one can strive to place the Bragg Peak in or near the central plane of the field of view of the gamma camera so as to obtain an optimal output of the gamma camera. The target is then preferably not moved in the Z-direction during the session, so as to maintain a fixed position relative to the beam apparatus, and the collimator (or entire gamma camera) is moved in Z-direction. For example this can be used to locate the Bragg peak by moving the gamma camera along the Z-direction, e.g. during a verification process on a phantom.

In an embodiment the Z-axis drive for the collimator or gamma camera is linked to the control system, wherein the radiation session control data includes data representing one or more planned beam penetration depths of a radiation session to be performed, as well as data representing one or more planned collimator Z-axis positions for the Z-axis drive, e.g. said radiation session control data including data representing a pattern of Z-axis motion of the collimator, preferably the gamma camera including the collimator, in synchronicity with a planned pattern of varying beam penetration depth for the radiation session to be performed, e.g. so as to allow the Bragg peak of the emitted radiation beam to be located in or close to a central plane of the collimator which is a plane of geometrical symmetry through the slit aperture of the collimator.

In an embodiment wherein there is provision for a Z-axis drive of the gamma camera, one can envisage that the gamma camera can be positioned in Z-direction so as to achieve that the central group is arranged at the determined or planned Z-axis position of the Bragg Peak.

In an embodiment the scintillation elements of an array each have an incident face, said incident faces being located in a common flat plane, preferably a plane perpendicular to the central plane of the collimator, which is a plane of geometrical symmetry through the slit aperture of the collimator. This allows for a practical embodiment of the detector.

In an advantageous embodiment the scintillation elements of said an each have an incident face, said incident faces being located in a common concave plane.

Preferably each scintillation element has an imaginary main plane corresponding to a geometrical plane of symmetry in the direction of the height of the scintillation element, and the scintillation elements of an array are arranged in a fanned arrangement with each scintillation element oriented so that its respective imaginary main plane extends through the slit aperture of the collimator. In this design each scintillation element is directed at the slit aperture of the collimator, thereby avoiding or reducing depth of interaction (DOI) effects that may be detrimental to the accuracy of the gamma camera.

In an embodiment thereof each scintillation element has an increasing width from the incident face towards a rear face opposite the incident face.

As the length of the slit aperture of the collimator may in some designs be substantial, e.g. between 15 and 35 centimeters in an embodiment for use in radiation of the human head, one can envisage an embodiment wherein the detector of the gamma camera has multiple arrays of longitudinal scintillation elements with the incident faces of said scintillation elements in a common plane, preferably strips of solid scintillation material, the scintillation elements of said multiple arrays being aligned on common lines parallel to the collimator slit aperture. For example the detector may consist of two such arrays next to one another, or even more than two such arrays thereby allowing a further reduction of the length of each scintillation element, e.g. four or more arrays of scintillation elements. The increase of the number of arrays e.g. allows for the use of relatively slow and attractively priced scintillator elements compared to a design with a single array.

In an embodiment the gamma camera may have multiple, e.g. two, arrays of scintillation elements in a stacked arrangement, wherein the incident faces of scintillation members of one array are oriented towards the rear faces over scintillation elements of an overlying array, preferably said scintillation elements embodied as strips of solid scintillation material.

In a preferred embodiment the collimator has opposed longitudinal edges embodied as knife edges, preferably having an opening angle of at most 50°, preferably at least most 40°, e.g. approximately 30°.

In an embodiment the slit width actuator mechanism is adapted for variation of the slit width to a minimum width of at least 1 millimeters, e.g. with a maximum width of 10 millimeters.

In an embodiment the detector has—in a direction perpendicular to the collimator slit—an effective width of at least 25 centimeters, preferably at least 35 centimeters, e.g. approximately 50 centimeters. This allows to place the detector relatively far away from the collimator slit, thereby benefiting from the magnification effect and enhancing the accuracy of the gamma camera. In an embodiment the detector may have an effective length equal or greater than the slit, e.g. a length between 15 and 35 centimeters. Such a rather large detector is considered advantages for use in an installation where the target may be a human head for the treatment of head tumors etc.

In an embodiment the target support is a patient head support for supporting the head of a patient.

In an embodiment the target support is a human patient table including a head support adapted to support the patient inclusive the head.

In a practical embodiment the installation comprises a support structure for the gamma camera that is adapted to support the gamma camera at a distance vertically above the target support, e.g. adapted to support the gamma camera at least 20 centimeters above a head support of the installation, e.g. the support structure being adjustable in height.

According to a third aspect thereof the invention relates to a hadron radiation installation adapted to subject a target to irradiation by a hadron radiation beam, said installation comprising:
- a target support configured to support a target;
- a hadron radiation apparatus adapted to emit a hadron radiation beam along a beam axis to irradiate the target supported by the target support, said radiation beam penetrating into the target, wherein the radiation apparatus has a control system at least comprising a beam penetration depth control allowing at least to control and vary the penetration depth of the radiation beam into the target,
- a radiation beam range sensor device adapted to determine the penetration depth of said radiation beam into the target, wherein said range sensor device comprises a gamma camera responsive to prompt gamma rays that are emitted while said radiation beam penetrates into the target, said gamma camera comprising:
- a collimator having a wall that blocks gamma radiation and an aperture in said wall,
- a detector comprising one or more scintillation elements (24) upon which gamma radiation passing through said aperture of the collimator is incident,
- an electronic readout mechanism associated with said detector, wherein the collimator of the gamma camera is a slit collimator having an elongated slit aperture, which is characterized in that the detector of the gamma camera comprises an array of multiple elongated scintillation elements in parallel and side-by-side arrangement, each scintillation element having a length along a longitudinal axis that is parallel to the collimator slit aperture, a width perpendicular to said length and parallel to an incident face of said scintillation element, and a height perpendicular to said length and perpendicular to an incident face of said scintillation element, and in that the scintillation elements in a central group of scintillation elements of said array each have a smaller width than the width of individual scintillation elements in end groups of scintillation elements between which end groups said central group is located.

As explained above this arrangement allows for greater accuracy of the detector of the gamma camera, thereby rendering it more suitable for real-time feedback purposes than prior art proposals.

In a preferred embodiment of the third aspect of the invention the gamma camera is movably supported relative to the radiation apparatus so as to be movable, with the slit aperture substantially perpendicular to the beam axis, in a Z-axis direction substantially parallel to the beam axis without moving the target support relative to said proton beam apparatus, preferably over a length of at least 20 centimeters, and wherein a Z-axis drive is provided to controllable move the gamma camera in said Z-axis direction. As explained above this allows to position the gamma camera at the optimal Z-position for detection of the beam penetration depth.

In a preferred embodiment the Z-axis drive is linked to the control system, wherein said radiation session control data includes data representing one or more planned beam penetration depths of a radiation session to be performed, as well as data representing one or more planned collimator Z-axis positions for the Z-axis drive, e.g. said radiation session control data including data representing a pattern of Z-axis motion of the collimator, preferably the gamma camera including the collimator, in synchronicity with a planned pattern of varying beam penetration depth for the radiation session to be performed, preferably so as to allow the Bragg peak of the emitted radiation beam to be located in a central plane of the collimator which is a plane of geometrical symmetry through the slit aperture of the collimator.

A fourth aspect of the invention relates to an installation according to the preamble of claim 18, a hadron radiation installation adapted to subject a target to irradiation by a hadron radiation beam, said installation comprising:
- a target support configured to support a target;
- a hadron radiation apparatus adapted to emit a hadron radiation beam along a beam axis to irradiate the target supported by the target support, said radiation beam penetrating into the target, wherein the radiation apparatus has a control system at least comprising a beam penetration depth control allowing at least to control and vary the penetration depth of the radiation beam into the target,
- a radiation beam range sensor device adapted to determine the penetration depth of said radiation beam into the target, wherein said range sensor device comprises a gamma camera responsive to prompt gamma rays that are emitted while said radiation beam penetrates into the target, said gamma camera comprising:
- a collimator having a wall that blocks gamma radiation and an aperture in said wall,
- a detector comprising one or more scintillation elements upon which gamma radiation passing through said aperture of the collimator is incident,
- an electronic readout mechanism associated with said detector, wherein the collimator of the gamma camera is a slit collimator having an elongated slit aperture, the slit aperture having non-parallel faces defining an opening angle of the slit aperture and a corresponding field of view, which is characterized in that the radiation beam range sensor device comprises one or more gamma cameras that provide multiple slit apertures at axially spaced positions relative to the beam axis, the axial spacing between successive slit apertures being at least 3 centimeters, preferably at most 10 centimeters, each slit aperture providing a field of view having an opening angle, which field of view is intersected by the pencil beam in operation of the installation, the fields of view provided by successive slit apertures adjoining one another, preferably partly and non-completely overlapping, so as to establish a continuous field of view along a section of the beam axis.

The provision of multiple slit apertures each providing a field of view having an opening angle at said axial positions may allow for an increase of the length of the imaged section along the beam axis. More importantly this measure allows for a design of each individual slit aperture so as to have a limited or reduced opening angle compared to the use of a single camera to observe the same section of beam axis, e.g. an opening angle of at most 30°, e.g. at most 20°, e.g. with a minimal opening angle of at least 10°. Reduction of the opening angle through the use of multiple slit aperture at axially spaced apart locations advantageously entails increased resistance of the collimator against edge penetration, and thereby enhances the imaging of the beam section by the beam range sensor device.

In the fourth aspect of the invention, preferably, all slit apertures of the beam range sensor device are fixed width slit apertures. If desired however, one or more of said slit apertures can be embodied as variable width slit apertures as discussed with reference to the first aspect of the invention.

In a practical embodiment of the fourth aspect of the invention, the radiation beam range sensor device has 2 to 6 slit apertures, e.g. 2 or 3 slit apertures.

Preferably in the fourth aspect of the invention all slit apertures of the beam range sensor device are oriented substantially perpendicular to the beam axis.

In a practical embodiment of the fourth aspect of the invention the beam range sensor device comprises multiple gamma cameras, each gamma camera having a single slit aperture, preferably a fixed slit width slit aperture. This allows for a relative simple and compact design of each camera, e.g. facilitating the manufacturing thereof as well as the integration into the beam range sensor device. Also maintenance can be facilitated by the use of this design.

In a practical embodiment of the fourth aspect of the invention the multiple slit apertures—when seen in a plane transversely to the beam axis—e.g. in an embodiment with multiple gamma cameras each having one or more, e.g. a single, slit apertures-are arranged at different angular positions relative to the beam axis, in practice to the target support. For example one gamma camera is below the target support and one angled upward from a left-hand side and one angled upward from a right-hand side. For example multiple gamma cameras, e.g. three or more, are supported by a camera support device in a helical arrangement relative to the beam axis. The arrangement of multiple gamma cameras at different angular positions, e.g. along a helical path about the beam axis, or at least along a section of the helical path, allows e.g. for the use of cameras with relatively large detectors, yet with their slit apertures relatively close together in axial direction of the beam axis according to the fourth aspect of the invention.

In an embodiment of the fourth aspect of the invention the installation comprises a gamma camera support device supporting multiple gamma cameras, said support device being adapted to allow for adjustment of one or more camera positions relative to the beam axis causing adjustment of the overlap of their fields of view, e.g. one or more of the gamma cameras being axially adjustable relative to one another and/or one or more cameras being rotatable about a rotation axis, e.g. an axis transverse to the beam axis allowing to pivot one or more gamma camera so as to alter their orientation and overlap of their fields of view.

In an embodiment of the fourth aspect of the invention the beam range sensor device comprises at least one gamma camera, possibly only has a single one gamma camera, that has multiple slit apertures at said axially spaced positions according to the fourth aspect of the invention.

A fifth aspect of the invention relates to a hadron radiation installation adapted to subject a target to irradiation by a hadron radiation beam, said installation comprising:
 a target support configured to support a target;
 a hadron radiation apparatus adapted to emit a hadron radiation beam along a beam axis to irradiate the target supported by the target support, said radiation beam penetrating into the target,
wherein the radiation apparatus has a control system at least comprising a beam penetration depth control allowing at least to control and vary the penetration depth of the radiation beam into the target,
 a radiation beam range sensor device adapted to determine the penetration depth of said radiation beam into the target, wherein said range sensor device comprises a gamma camera responsive to prompt gamma rays that are emitted while said radiation beam penetrates into the target,
said gamma camera comprising:
 a collimator having a wall that blocks gamma radiation and an aperture in said wall,
 a detector comprising one or more scintillation elements upon which gamma radiation passing through said aperture of the collimator is incident,
 an electronic readout mechanism associated with said detector,
wherein the collimator of the gamma camera is a slit collimator having an elongated slit aperture, the slit aperture having non-parallel faces defining an opening angle of the slit aperture and a corresponding field of view,
which is characterized in that the slit aperture is formed by two spaced apart collimator main wall portions, each defining an outer side face of the slit aperture, and an elongated collimator wall rod member of radiation blocking material, which rod member is arranged in between and spaced from said two spaced apart main wall portions to form a first and second slit passage of the slit aperture, said rod member defining inner side faces that each bound in combination with an adjacent outer side face one of said slit passages, the inner and outer side faces bounding each slit passage being non-parallel and defining an opening angle and corresponding field of view of the slit passage, each slit passage having a central plane of maximum transmission, the central planes of said first and second slit passage being non-parallel and intersecting one another, preferably intersecting between the collimator and the beam axis, so the fields of view of the slit passages overlap partly and in combination define a total field of view of the slit aperture.

In this design the first and second slit passages, and possibly one or more central slit passages when present, effectively allow to mimic an ordinary singular slit passage type slit aperture. The advantage of the inventive slit aperture design lies mainly in the ability to counteract the problem of penetration of gamma radiation through portions, mainly edge portions, of the collimator along the boundaries of the slit aperture or slit passages. Effectively an ordinary slit aperture having a particular opening angle can be replaced by the inventive design with the advantage that now the collimator portions bounding the longitudinal sides of each slit passage can be made less penetrable for gamma radiation, with resulting enhancement of the quality and/or efficiency of the imaging of the penetration of the pencil beam into the target. The fifth aspect of the invention also may be done with thick collimator walls, e.g. having a thickness greater than 30 millimeters, e.g. greater than 40 or even greater than 80 millimeters.

In a practical embodiment the outer side faces of the slit aperture of the collimator have parallel outer side face portions at the side of the collimator remote from the detector and have diverging outer side face portions at the side facing the detector—when seen in the direction of the beam axis towards the detector of a gamma camera—, and the collimator wall rod member has diverging inner side face portions at the side of collimator remote from the detector and parallel inner side face at the side facing the detector.

In an embodiment the diverging inner side face portions of the rod member join one another at an apex.

In a practical embodiment the first and second slit passages are shaped to have equal opening angles.

In a practical embodiment the first and second slit passages are shaped as mirror imaged passages relative to a plane of symmetry that is located centrally between the slit passages.

The fifth aspect of the invention allows for a design of the slit passages such that a gamma radiation image emanating from the field of view of a first slit passage does not overlap on the detector with a gamma radiation image emanating from the field of view of the second slit passage.

In a practical embodiment a blunt edge angle is present in an outer side face of each main wall part having an angle which is equal or greater than 150°, preferably between 155 and 170°.

In a further variant of the fifth aspect of the invention not a single one rod member is envisaged in the slit aperture—which is practically preferred—but multiple elongated collimator wall rod members are arranged in between said two spaced apart main wall portions and parallel to one another to form one or more central slit passages in addition to said first and second slit passages, preferably each central slit passages being bounded by non-parallel faces of neighbouring wall rod members and defining an opening angle and corresponding field of view of the central slit passage, the fields of view of the slit passages overlapping partly and in combination defining the field of view of the slit aperture.

It will be appreciated that any detail of the gamma camera, collimator, and/or detector discussed herein with reference to any of the first, second, and/or third aspect of the invention can equally be applied in combination with a gamma camera according to the fourth and/or fifth aspect of the invention unless technically impossible. For instance a fanned arrangement of detector segments can be applied in combination with the fourth and/or fifth aspect of the invention, e.g. with a concave incident surface of the detector facing each slit aperture. Or for example a variable slit width can be applied in combination with the fourth and/or fifth aspect of the invention.

In general it will be appreciated that any of the optional or preferred features discussed herein with reference to one aspect of the invention may also be combined with any of the other aspects of the present invention. Some of those combinations are discussed herein in more detail.

The present invention also relates to a gamma camera as described herein for use in combination with a hadron radiation apparatus.

The present invention also relates to the use of a gamma camera as described herein in a hadron radiation installation.

The present invention also relates to a gamma camera, or multiplicity of gamma cameras, or collimator, and methods of use thereof as described herein for other purposes than in a hadron radiation installation. For example the present invention envisages a system and/or method for gamma radiation emission imaging of a non-human animal or part thereof, e.g. mouse or a rat, or of a human, the non-human animal or human containing a gamma ray emitting tracer compound, said system and/or method comprising or making use of a gamma camera, or multiplicity of gamma cameras, or collimator, and methods of use thereof as described herein. In such a system a target support may be provided, yet a hadron radiation apparatus and a radiation beam sensor device as mentioned herein are absent. Yet any gamma cameras described herein with reference to the radiation beam sensor device may be present for imaging. The beam axis mentioned herein may e.g. then be an axis, e.g. a longitudinal axis, of an object space in which the animal or human is held during imaging.

The present invention also relates to a method for hadron radiation therapy verification using a hadron radiation installation according to one or more aspects of the invention, wherein a target embodied as a phantom is subjected in a radiation session to irradiation by a hadron radiation beam, said method comprising:
arranging the phantom on the target support, preferably immobilizing the phantom on the target support;
operating the radiation apparatus to emit a hadron radiation beam along a beam axis to irradiate the phantom supported by the target support, said radiation beam penetrating into the phantom,
determining with the radiation beam range sensor device the actual penetration depth of said radiation beam into the phantom.

In an embodiment of the method use is made of an installation wherein the control system is adapted to input and store in a memory one or more sets of radiation session control data corresponding to one or more radiation sessions to be performed with the radiation beam apparatus, wherein the collimator is embodied at least according to the first aspect of the invention and has a slit width actuator mechanism that is linked to the control system, and wherein the verification radiation session is performed on the basis of stored radiation session control data including data representing a pattern of varying beam penetration depth during the session,
and wherein the verification radiation session is performed on the basis of stored radiation session control data including data representing a pattern of variation of the slit width of the collimator to be performed in synchronicity with the varying beam penetration depth pattern.

In an embodiment of the method the verification radiation session is performed on the basis of stored radiation session control data including data representing a pattern of Z-axis motion of the collimator, preferably the gamma camera including the collimator, in synchronicity with the planned pattern of varying beam penetration depth for the radiation session to be performed, preferably so as to allow the Bragg peak of the emitted radiation beam to be located in a central plane of the collimator which is a plane of geometrical symmetry through the slit aperture of the collimator.

The invention also relates to a method for determination of penetration depth of a hadron beam into a target, wherein use is made of a radiation beam range sensor device as described herein.

The invention also relates to a method for imaging a hadron beam penetrating into a target irradiated by a hadron radiation beam, wherein use is made of a radiation beam range sensor device, or gamma camera, or multiplicity of gamma cameras as described herein.

The invention will now be explained with reference to the drawings.

BRIEF DESCRIPTION OF THE DRAWINGS

FIG. 1 shows schematically a proton radiation therapy installation according to the invention, FIG. 5 shows schematically a beam range sensor device with multiple gamma cameras arranged at axially spaced positions along the beam axis, FIG. 6 shows schematically in cross section a beam range sensor device with multiple gamma cameras arranged at axially spaced positions along the beam axis, one or more of the cameras being adjustable allowing to adapt the overlap of the fields of view of successive cameras, FIG. 7 shows schematically in cross section a beam range sensor device embodied as a single gamma camera having multiple slit apertures at axially spaced positions along the beam axis, FIG. 8 shows schematically, in a view on a plane transverse to the beam axis, a helical arrangement of multiple gamma cameras that are in said plane at angular different orientations relative to be beam axis and at axially spaced locations along the beam axis.

DETAILED DESCRIPTION OF THE INVENTION

Figure 3:
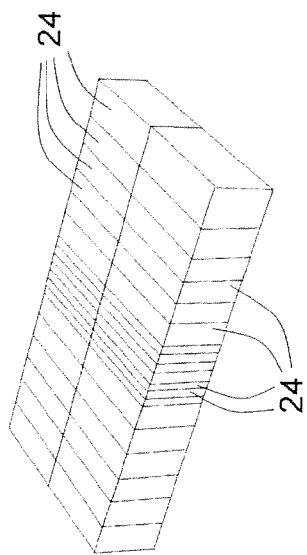
FIG. 3 shows schematically an alternative embodiment of a scintillation elements array of the gamma camera according to the invention.

With reference to FIG. 1 an example of a proton radiation therapy installation adapted to subject a target to irradiation by a proton radiation beam according to the invention will be discussed below. It is noted that the invention equally applies to radiation installation emitting beams with other hadrons, e.g. carbon-ions.

The installation comprises a target support 1 configured to support, preferably immobilize, a target 2. In this example the target support is a patient head support for supporting the head of a patient or a phantom representing a human head. The head support here forms part of a human patient table 3 adapted to support the human patient (not shown) inclusive the head.

For example the target 2 is a 20 centimeter diameter sphere of brain tissue according to ICRU specifications.

The installation comprises a proton radiation apparatus 10 adapted to emit a pencil type proton radiation beam 11 along a beam axis (Z-axis) to irradiate the target 2 supported by the target support 1. This proton radiation beam 11 penetrates into the target 2.

As is known the apparatus 10 is preferably embodied to perform the spot scanning technique where a pencil type proton beam 11 is stepped over the tumor, e.g. using beam steering magnets.

As explained a Bragg Peak is present at the end of the proton track in the target 2.

Here it is shown that the beam 11 passes through a degrader 12, e.g. of polyethylene.

In this example the degrader 12 is held in a tube structure 13 adapted to slow down any neutrons generated in the degrader 12.

The radiation apparatus 10 has a control system 15, commonly a computerized control system.

The control system 15 at least comprises a beam penetration depth control, e.g. including a dedicated software program installed in said computerized control system, allowing at least to control and vary the penetration depth of the beam 11 into the target 2.

The installation comprises a radiation beam range sensor device 17 that is adapted to determine the penetration depth of the beam 11 into the target 2. This range sensor device comprises a gamma camera 20 responsive to prompt gamma rays that are emitted due to the beam 11 penetrating into the target 2.

In this example, the gamma camera 20 comprises:
- a collimator 21 having a wall that blocks gamma radiation and an aperture 22 in said wall;
- a detector having one or more scintillation elements 24 that convert gamma radiation passing through said aperture of the collimator 21 and incident on the one or more scintillation elements into optical radiation;
- one or more photodetectors (not shown) adapted to detect said optical radiation;
- an electronic readout mechanism associated with said detector.

In a simple embodiment the readout mechanism primarily functions as a gamma counter (not shown) connected to said one or more photodetectors and providing a gamma count signal.

The collimator of the gamma camera 20 is a slit collimator having an elongated slit aperture 22.

The slit aperture 22—as is preferred when a one-dimensional type detector is used—here is arranged substantially perpendicular to the beam axis of beam 11. It is noted that a perfect perpendicular alignment of the slit may not be necessary at all times, e.g. allowing for small changes of the beam orientation during a session without adjusting the position of the collimator/gamma camera to maintain a perfect perpendicular alignment.

It is noted that for a two-dimensional type detector the orientation of the slit perpendicular to the beam is in principal not a necessity.

The collimator 21 is a variable width slit collimator having an elongated slit aperture 22 of variable. The collimator has first collimator member 21*a* and a second collimator member 21*b* that each define one of the opposed longitudinal edges of the slit aperture 22.

As is preferred the longitudinal edges are embodied as knife edges, providing an opening angle of at most 50°, preferably at least most 40°, e.g. approximately 30°.

The collimator 21 has a slit width actuator mechanism 23 for displacing and positioning said collimator members 21*a, b* relative to one another so as to allow for different slit widths.

The radiation beam range sensor device 17 is linked to a monitoring system, e.g. including a display 30, of the proton radiation apparatus to provide at least beam penetration depth information, preferably during a radiation session.

The radiation beam range sensor device is also linked to the beam penetration depth control of the control system 15 to provide at least beam penetration depth feedback data to the beam penetration depth control.

In an embodiment the radiation beam range sensor device is adapted to control the slit width actuator mechanism 23 in dependency of the actual gamma count rate. In a variant the radiation beam range sensor device is adapted to control the slit width actuator mechanism 23 so as to increase the slit width if the actual gamma count rate is below a predetermined lower threshold, and to decrease the slit width if the actual gamma count rate is above a predetermined upper threshold, said upper threshold representing a higher gamma count rate than the lower threshold.

The control system 15 here is adapted to input, via input device 31, and store in a memory one or more sets of radiation session control data corresponding to one or more radiation sessions to be performed with the radiation beam apparatus.

As can be seen the slit width actuator mechanism 23 of the collimator 21 is linked to the control system 15.

In an embodiment the radiation session control data includes data representing one or more planned beam penetration depths of a radiation session to be performed, e.g. a pattern of varying beam penetration depth.

In an embodiment the radiation session control data includes data representing one or more planned slit widths of the collimator 21 for a radiation session to be performed, e.g. a pattern of variation of the slit width of the collimator 21 to be performed in synchronicity with the varying beam penetration depth pattern.

In the installation, as is preferred, the apparatus 10 includes a beam directing device (not shown) which is adapted—as is known in the field-to vary the position and orientation of the beam axis relative to the target support 1. For example the beam axis can be moved in multiple degrees of freedom, e.g. by a two-axis mechanism (e.g. vertical and horizontal) relative to the target support and/or by an angular motion mechanism to orient the beam at various angular orientations relative to the target support. The beam directing device allows to direct the proton beam as desired.

The apparatus 10 is also embodied to vary the penetration depth of the proton beam into the target 2, e.g. by variation of the beam power.

The apparatus 10 allows to locate the Bragg Peak of the emitted pencil type proton radiation beam at a planned location at least represented by X, Y, Z coordinates relative to the gamma camera, wherein the Z-coordinate is along the beam axis and the X and Y coordinates are along orthogonal axes in a plane perpendicular to the beam axis.

As is preferred, the control system 15 is adapted to input and store in a memory one or more sets of radiation session control data corresponding to one or more radiation sessions to be performed with the radiation beam apparatus, wherein said radiation session control data includes data representing a planned pattern of X-Y motion of the pencil type radiation beam of a radiation session to be performed.

As is preferred, the stored radiation session control data includes data representing a planned pattern of variation of the slit width of the collimator in synchronicity with the planned pattern of X-Y motion of the radiation beam for radiation session to be performed.

In FIG. 1 it is illustrated that the gamma camera 20 including the collimator 21 is movably supported, here on a linear guide 35, relative to the proton radiation apparatus 10 so as to be movable, here with the slit aperture 22 substantially perpendicular to the beam axis, in a Z-axis direction substantially parallel to the beam axis without moving the target support relative to said proton beam apparatus. As is preferred the motion range of the gamma camera in said direction is at least 20 centimeters, e.g. allowing to move the collimator 21 over the head whilst the patient itself is not moved.

As is preferred the gamma camera 20 is supported such that its perpendicular orientation with respect to the beam axis is maintained even when the beam axis changes orientation, e.g. its angular orientation.

A Z-axis drive 18 is provided to controllable move the gamma camera 20 including the collimator, in Z-axis direction.

As is preferred the Z-axis drive 18 is linked to the control system 15.

In an embodiment the radiation session control data includes data representing one or more planned beam penetration depths of a radiation session to be performed, as well as data representing one or more planned collimator Z-axis positions for the Z-axis drive 18, e.g. said radiation session control data including data representing a pattern of Z-axis motion of the gamma camera 20 including the collimator, in synchronicity with a planned pattern of varying beam penetration depth for the radiation session to be performed, preferably so as to allow the Bragg peak of the emitted radiation beam to be located in a central plane 26 (see FIG. 4) of the collimator 21 which is a plane of geometrical symmetry through the slit aperture 22 of the collimator.

As can be seen in FIG. 1 the installation comprises a support structure for the gamma camera that is adapted to support the gamma camera at a distance vertically above the target support, e.g. adapted to support the gamma camera with its collimator at least 20 centimeters above a head support 1 of the installation.

If desired (not shown here) the support structure can be embodied to be adjustable in height so that the gamma camera 20 is movable in a Y-axis direction, that is substantially perpendicular to the beam axis without moving the target support relative to the beam apparatus. A Y-as drive is then preferably provided to controllably move the gamma camera in said Y-axis direction. The Y-as direction motion may advantageously be used to keep the collimator at a desired distance from the beam axis, e.g. to maintain a desired geometrical magnification obtained by the ratio between the collimator-detector distance on the one hand and the collimator-beam axis distance on the other hand. For example if a radiation session involves substantial motion of the beam in Y-axis direction (e.g. in a scanning process over a treatment field) the gamma sensor 20 may be moved in said Y-axis direction is a synchronous pattern.

In a practical embodiment, e.g. for brain tumor treatment, the gamma sensor is arranged to have a field of view that intersects the beam axis over a length (in Z-direction) of between 5 and 10 centimeters, e.g. about 7 centimeters.

In a practical embodiment the detector is operated to detect gamma ray energies are above 1.5 MeV.

As is preferred the detector of the gamma camera 20 comprises an array of multiple elongated scintillation elements 24 in parallel and side-by-side arrangement.

Each scintillation element 24 has a length along a longitudinal axis that is parallel to the collimator slit aperture 22, a width perpendicular to said length and parallel to an incident face of said scintillation element, and a height perpendicular to said length and perpendicular to an incident face of said scintillation element. As is preferred said length is greater than each of said width and said height. In a practical embodiment the length of each element 24 is at least 5 times the width of the element.

In a practical embodiment the scintillation elements 24 each are embodied as an elongated strip of solid scintillation material, each strip having an incident face, a rear face opposite the incident face, side faces, and end faces at longitudinal ends of the strip.

A photodetector is connected to an end face of the strip, e.g. directly or via a light guide, e.g. via a light guide fibre leading to a suitable photodetector.

It is envisaged that in order to provide suitable feedback on the basis of a gamma count signal in practice the gamma count rate may be in the range between 1 and 10 million counts/sec. It is further envisaged that in a practical embodiment each scintillation element of the detector may be designed for a maximum of 30.000 counts/secs.

As can be seen in FIGS. 1-4 it is possible that in an array the scintillation elements in a central group of scintillation elements of the array each have a smaller width than the width of individual scintillation elements in end groups of scintillation elements between which end groups said central group is located.

Figure 2:
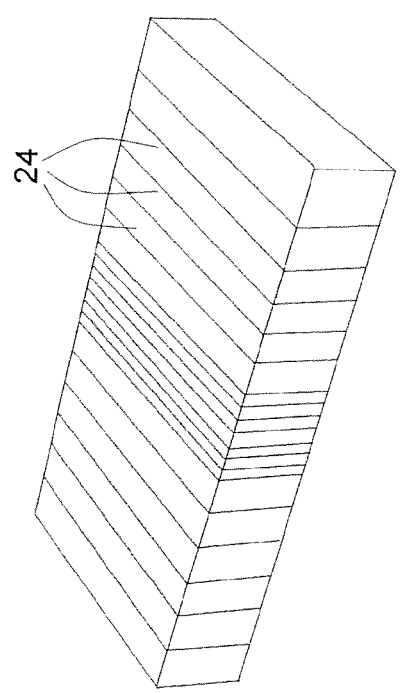
FIG. 2 shows schematically an embodiment of a scintillation elements array of the gamma camera according to the invention.

In the embodiments of FIGS. 1-3 it is shown that the scintillation elements of an array each have an incident face, said incident faces being located in a common flat plane, preferably a plane perpendicular to the central plane 26 of the collimator, which is a plane of geometrical symmetry through the slit aperture of the collimator.

Figure 4:
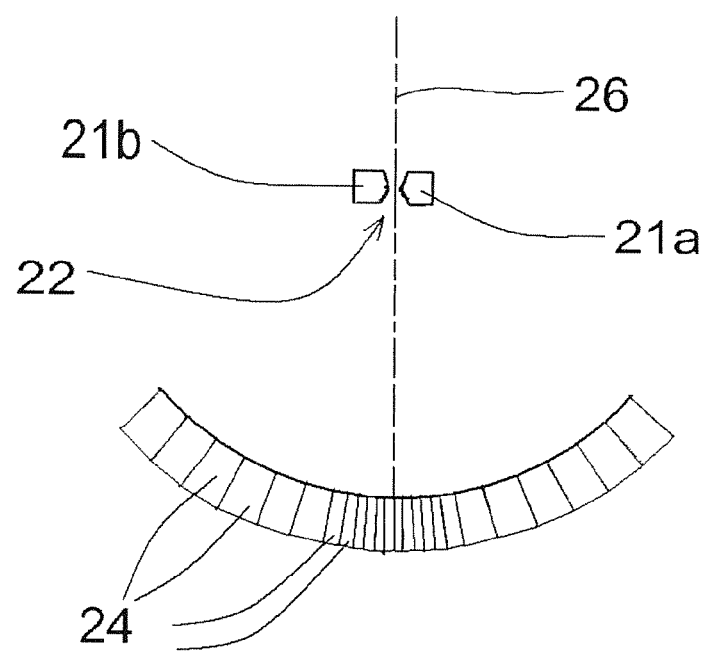
FIG. 4 shows schematically a slit collimator and embodiment of a scintillation elements array of the gamma camera according to the invention.

In FIG. 4 it is shown that the scintillation elements of an array each have an incident face, said incident faces being located in a common concave plane.

More in particular FIG. 4 illustrates the design wherein each scintillation element 24 has an imaginary main plane corresponding to a geometrical plane of symmetry in the direction of the height of the scintillation element, and wherein the scintillation elements of the array are arranged in a fanned arrangement with each scintillation element oriented so that its respective imaginary main plane extends through the slit aperture 22 of the collimator 21.

If desired one or more scintillation elements are embodied such that a scintillation element has an increasing width from the incident face towards a rear face opposite the incident face.

It is noted that the fanned arrangement of the scintillation elements as illustrated in FIG. 4 is also possible with a planar design of the detector, e.g. with all incident faces of the elements 24 lying in a common flat plane.

The fanned arrangement can be embodied with the width of a central group of scintillation elements being smaller than of elements in end groups, but can also be done with all scintillation elements having equal widths.

FIG. 3 illustrates the measure that the detector has multiple arrays of scintillation elements 24 with the incident faces of said scintillation elements in a common plane, preferably strips of solid scintillation material, the scintillation elements of said multiple arrays being aligned on common lines parallel to the collimator slit aperture.

In an embodiment that is not shown the detector has multiple arrays of scintillation elements in a stacked arrangement, wherein the incident faces of scintillation members of one array are oriented towards the rear faces over scintillation elements of an overlying array, preferably said scintillation elements embodied as strips of solid scintillation material.

It is preferred for a radiation shield 38, e.g. of lead, to be placed opposite from the gamma camera, here below, at the other side of the target support 1, here, as is preferred on the floor 39 of a treatment chamber.

It will be appreciated that the installation as shown here allows to perform a method for hadron radiation therapy verification, wherein the target 2 embodied as a phantom is subjected in a radiation session to irradiation by a radiation beam.

This verification method may comprises:
arranging the phantom 2 on the target support 1, preferably immobilizing the phantom on the target support 1;
operating the proton radiation apparatus 10 to emit a pencil type proton radiation beam along a beam axis to irradiate the phantom 2 supported by the target support, said proton radiation beam penetrating into the phantom,
determining with the radiation beam range sensor device 17 the actual penetration depth of said proton radiation beam into the phantom target 2.

In an embodiment a verification method may comprise performing the verification radiation session on the basis of stored radiation session control data including data representing a pattern of varying beam penetration depth during the session, and on the basis of stored radiation session control data including data representing a pattern of variation of the slit width of the collimator to be performed in synchronicity with the varying beam penetration depth pattern.

In an embodiment a verification method may comprise performing the verification radiation session on the basis of stored radiation session control data including data representing a pattern of varying beam penetration depth during the session, and on the basis of stored radiation session control data including data representing a pattern of Z-axis motion of the gamma camera 20 in synchronicity with the planned pattern of varying beam penetration depth for the radiation session to be performed, preferably so as to allow the Bragg peak of the emitted radiation beam to be located in a central plane of the collimator which is a plane of geometrical symmetry through the slit aperture of the collimator.

FIG. 5 shows schematically a beam range sensor device 17' with multiple gamma cameras 20' that are arranged at axially spaced positions along the beam axis 11 in a manner according to the fourth aspect of the invention.

Each camera 20' here has a single, preferably fixed width, slit aperture 22 offering an opening angle and associated field of view represented by diverging lines from the slit aperture 22 towards the beam axis 11.

Each camera 20' has its dedicated detector 24 here shown as embodied in a manner as discussed with reference to FIG. 4. The space between the detector 24 and the corresponding slit aperture 22 of a camera is shielded by radiation blocking walls from the outside and from the space of adjacent cameras.

The axial spacing between successive slit apertures 22 in the device 17' is at least 3 centimeters, preferably at most 10 centimeters, each slit aperture 22 providing a field of view having an opening angle, which field of view is intersected by the pencil beam in operation of the installation, the fields of view provided by successive slit apertures adjoining one another, preferably partly and non-completely overlapping, so as to establish a continuous field of view along a section of the beam axis.

As is preferred the fields of view of axially successive cameras 20' overlap one another in part so as to obtain a continuous total field of view of the device 17'.

The device 17' may be arranged in an installation as discussed with reference to FIG. 1 and replace the device 17 therein. Then, as is preferred, the Bragg Peak preferably lies in said section of the beam axis that is viewed by the multiple slit apertures.

In a practical embodiment the radiation beam range sensor 17' has 2 to 6 slit apertures, e.g. 2 or 3 slit apertures.

FIG. 6 illustrates the proposal to have a gamma camera support device 40 supporting multiple gamma cameras 20', wherein the support device is adapted to allow for adjustment of one or more camera positions relative to the beam axis 11 causing adjustment of the overlap of their fields of view. In this example each of the cameras 20' is mounted so as to be rotatable about an axis 41, here an axis transverse to the beam axis 11, allowing to pivot the gamma camera 20' so as to alter their orientation and thereby the overlap of their fields of view. The pivoting can here be done in direction of arrows P.

FIG. 7 illustrates the proposal to provide a beam range sensor device 17' with a camera 20" having multiple slit apertures 22 in a common collimator 21' as in the fourth aspect of the invention. It is shown, by way of example, that the detector is composed of multiple concave arrays of scintillation elements 24 as disclosed with reference to FIG. 4, each concave array being oriented towards a corresponding slit aperture 22 of the collimator. In another design the detector is flat and planar, yet a concave array (or set of adjoining arrays) is preferred.

FIG. 8 illustrates the proposal to provide the beam range sensor device 17'—when seen in a plane transversely to the beam axis 11—so that the slit apertures 22, here of multiple gamma cameras 20' each having a single slit aperture, are arranged at different angular positions relative to the beam axis and the target support 1 for target 2. Here one camera 20' is below the target support 1 and one angled upward from a left-hand side and one angled upward from a right-hand side. This is preferably obtained by arranging the multiple gamma cameras in a helical arrangement relative to the beam axis 11. It will be appreciated, e.g. by consideration of FIG. 1, that placing multiple cameras aligned on a line parallel to the beam axis leads to significant distances between the successive slits when, as is preferred, relatively large detectors are employed. The arrangement of cameras at different angular positions according to the fourth aspect of the invention allows to optimize the spacing between successive slit apertures whilst allowing for significant detector dimensions which enhances the imaging. As explained the provision of multiple slit apertures having an opening angle to image a section of the beam axis allows to reduce the opening angle of each individual slit aperture and thereby increase the resistance against edge penetration.

Figure 9A:
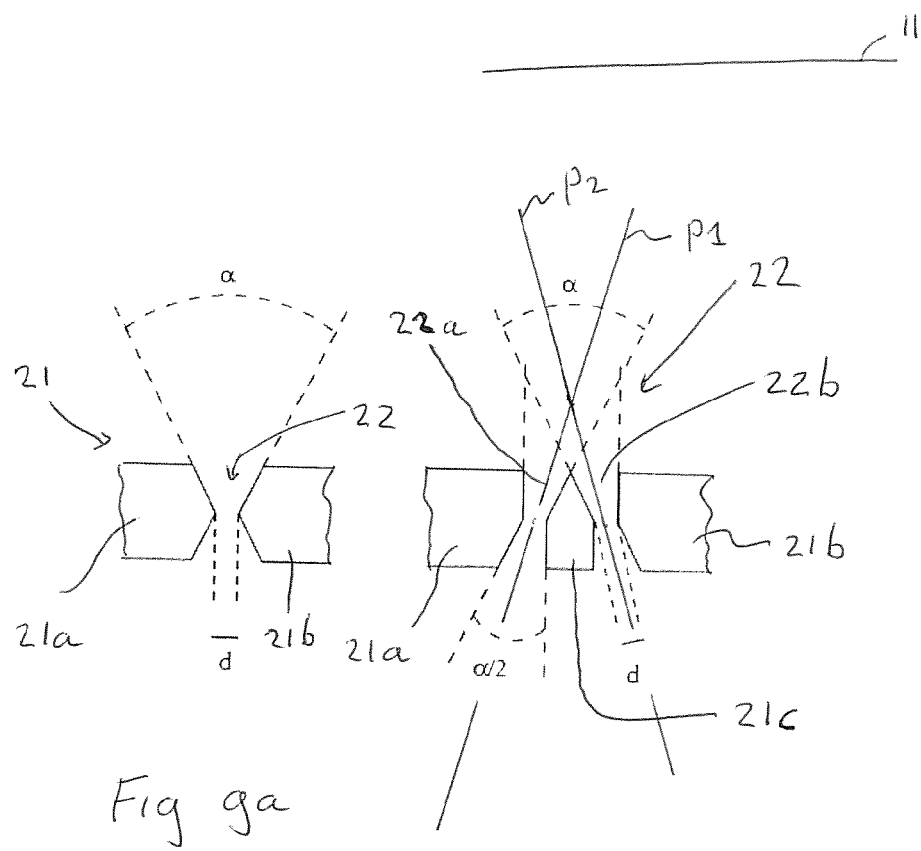
FIG. 9*a* shows—in cross-section—a portion of a collimator with a common singular slit passage type slit aperture.

FIG. 9a illustrates a common slit aperture 22 with a singular slit passage between opposed main wall portions 21a, 21b of collimator 21. The slit aperture has non-parallel faces providing an opening angle α and a knife-edge with smallest width d of the singular passage. As discussed with reference to the fifth aspect of the invention such a design may suffer in undesirable manner from edge penetration by gamma radiation leading e.g. to blurring of images and other quality issues of the imaging.

Figure 9B:
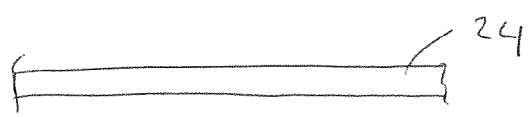
FIG. 9*b* shows—in cross-section—a portion of a collimator with a slit aperture according to the fifth aspect of the invention.

FIG. 9b illustrates a preferred embodiment of a collimator according to the fifth aspect of the invention that may be employed to replace e.g. the design of FIG. 9a and avoid or at least reduce the radiation penetration problem thereof.

In FIG. 9b the slit aperture 22 is formed by two spaced apart collimator main wall portions 21a, 21b, each defining an outer side face of the slit aperture, and an elongated collimator wall rod member 21c of radiation blocking material, which rod member 21c is arranged in between and spaced from said two spaced apart main wall portions 21a to form a first slit passage 22a and a second slit passage 22b of the slit aperture 22.

The rod member 21c defines inner side faces that each bound in combination with an adjacent outer side face one of the slit passages 22a, 22b. The inner and outer side faces that bound each slit passage 22a, 22b are non-parallel and define an opening angle α/2 and corresponding field of view of the slit passage 22a, 22b.

Each slit passage 22a, 22b has a central plane p1, p2 of maximum transmission, the central planes p1, p2 of the first and second slit passages 22a, 22b being non-parallel and intersecting one another, preferably intersecting between the collimator and the beam axis 11, so the fields of view of the slit passages overlap partly and in combination define a total field of view of the slit aperture.

The plane of maximum transmission p1 and p2 can be roughly equaled to, i.e. approximated by, a plane of geometrical symmetry of each slit passage.

As can be easily seen by comparing FIGS. 9a and 9b, the design of FIG. 9b allows for a design of the side faces of the slit passages that are much less easier to penetrate by gamma radiation whilst arriving at a similar opening angle field of view of the slit aperture 22.

In the preferred embodiment—when looking in the direction of the beam axis 11 towards the detector 24 of a gamma camera—the outer side faces of the slit aperture of the collimator have parallel outer side face portions at the side of the collimator remote from the detector and have diverging outer side face portions at the side towards the detector. The collimator wall rod member 21c has diverging inner side face portions at the side of collimator remote from the detector 24 and parallel inner side faces at the side towards the detector 24.

It can be seen that a blunt edge angle is present in an outer side face of each main wall part having an angle which is equal or greater than 150°, preferably between 155 and 170°.

In the FIG. 9 the first and second slit passages 22a, 22b are shaped to have equal opening angles.

In the FIG. 9 design the gamma camera is such that a gamma radiation image emanating from the field of view of the first slit passage 22a does not overlap on the detector 24 with a gamma radiation image emanating from the field of view of the second slit passage 22b.

In an embodiment that is not shown multiple elongated collimator wall rod members 21c are arranged in between said two spaced apart main wall portions 21a, 21b and parallel to one another to form one or more central slit passages in addition to said first and second slit passages, preferably each central slit passages being bounded by non-parallel faces of neighbouring wall rod members and defining an opening angle and corresponding field of view of the central slit passage, the fields of view of the slit passages overlapping partly and in combination defining the field of view of the slit aperture.

Aspects of the invention are described in the following numbered clauses which form part of the description.

1. A hadron radiation installation adapted to subject a target to irradiation by a hadron radiation beam, said installation comprising:
   a target support configured to support a target;
   a hadron radiation apparatus adapted to emit a hadron radiation beam along a beam axis to irradiate the target supported by the target support, said radiation beam penetrating into the target,
   wherein the radiation apparatus has a control system at least comprising a beam penetration depth control allowing at least to control and vary the penetration depth of the radiation beam into the target,
   a radiation beam range sensor device adapted to determine the penetration depth of said radiation beam into the target, wherein said range sensor device comprises a gamma camera responsive to prompt gamma rays that are emitted while said radiation beam penetrates into the target,
   said gamma camera comprising:
   a collimator having a wall that blocks gamma radiation and an aperture in said wall,
   a detector comprising one or more scintillation elements upon which gamma radiation passing through said aperture of the collimator is incident, and
   an electronic readout mechanism associated with said detector,
   wherein the collimator of the gamma camera is a slit collimator having an elongated slit aperture, wherein the collimator is a variable width slit collimator having an elongated slit aperture of variable width, said collimator comprising a first collimator member and a second collimator member that each define one of the opposed longitudinal edges of the slit aperture, said collimator having a slit width actuator mechanism for displacing and positioning said first and second collimator members relative to one another.

2. The installation according to clause 1, wherein the collimator is supported such that the slit aperture extends substantially perpendicular to the beam axis, and wherein the detector comprises an array of multiple elongated scintillation elements in parallel and side-by-side arrangement, each scintillation element having a length along a longitudinal axis that is parallel to the collimator slit aperture, a width perpendicular to said length and parallel to an incident face of said scintillation element, and a height perpendicular to said length and perpendicular to an incident face of said scintillation element, wherein said length is greater than each of said width and said height.

3. The installation according to clause 2, wherein the scintillation elements each are embodied as an elongated strip of solid scintillation material, each strip having an incident face, a rear face opposite the incident face, side faces, and end faces at longitudinal ends of the strip, wherein the scintillation elements convert the incident gamma rays into optical radiation, and wherein a photodetector is connected to an end face of the strip via a light guide fibre.

4. The installation according to clauses 2 or 3, wherein each scintillation element of the detector has an imaginary main plane corresponding to a geometrical plane of symmetry in the direction of the height of the scintillation element, and wherein the scintillation elements of said array are arranged in a fanned arrangement with each scintillation element oriented so that its respective imaginary main plane extends through the slit aperture of the collimator.

5. The installation according to one or more of the clauses 2-4, wherein the scintillation elements in a central group of scintillation elements of said array each have a smaller width than the width of individual scintillation elements in end groups of scintillation elements between which end groups said central group is located.

6. The installation according to one or more of clauses 2-5, wherein the scintillation elements of said array each have an incident face, said incident faces being located in a common flat plane.

7. The installation according to one or more of clauses 2-5, wherein the scintillation elements of said array each have an incident face, said incident faces being located in a common concave plane.

8. The installation according to one or more of the preceding clauses, wherein the radiation apparatus is adapted to vary the position and orientation of the beam axis relative to the target support, the radiation apparatus having an assembly of controllable magnets to steer the beam, and to vary the penetration depth into the target so as to locate the Bragg Peak of the emitted radiation beam at a planned location at least represented by X,Y,Z coordinates, wherein the Z-coordinate is along the beam axis and the X and Y coordinates are along orthogonal axes in a plane perpendicular to the beam axis.

9. The installation according to one or more of the preceding clauses, wherein the gamma camera is movably supported by a gamma camera support structure so as to be movable, preferably with the slit aperture substantially perpendicular to the beam axis, in a Y-axis direction that is substantially perpendicular to the beam axis without moving the target support relative to the beam apparatus, and wherein a Y-as drive is provided to controllably move the gamma camera in said Y-axis direction.

10. The installation according to one or more of the preceding clauses, wherein the collimator is movably supported by a gamma camera support structure so as to be movable in a Z-axis direction that is substantially parallel to the beam axis without moving the target support relative to beam apparatus and wherein a Z-axis drive is provided to controllable move the gamma camera including the collimator, in said Z-axis direction.

11. The installation according to clauses 9 or 10, wherein each of the Y-axis drive and/or Z-axis drive is linked to the control system, and wherein the control system is adapted to input and store in a memory one or more sets of radiation session control data corresponding to one or more radiation sessions to be performed with the radiation beam apparatus,
wherein said radiation session control data includes data representing one or more planned beam locations and/or penetration depths relative to the target for a radiation session to be performed, as well as data representing one or more planned Y-axis and/or Z-axis positions for the Y-axis and Z-axis drive respectively.

12. The installation according to at least clause 8, wherein the control system is adapted to input and store in a memory one or more sets of radiation session control data corresponding to one or more radiation sessions to be performed with the radiation beam apparatus, wherein said radiation session control data includes data representing a pattern of X-Y motion of the radiation beam for a radiation session to be performed,
and wherein said radiation session control data includes data representing a pattern of variation of the slit width of the collimator in synchronicity with the planned pattern of X-Y motion of the radiation beam for radiation session to be performed.

13. The installation according to one or more of the preceding clauses, wherein the control system is adapted to input and store in a memory one or more sets of radiation session control data corresponding to one or more radiation sessions to be performed with the radiation beam apparatus,
and wherein the slit width actuator mechanism of the collimator is linked to the control system,
and wherein said radiation session control data includes data representing one or more planned beam penetration depths of a radiation session to be performed,
and wherein said radiation session control data includes data representing one or more planned slit widths of the collimator for a radiation session to be performed.

14. A hadron radiation installation adapted to subject a target to irradiation by a hadron radiation beam, said installation comprising:
a target support configured to support a target;
a hadron radiation apparatus adapted to emit a hadron radiation beam along a beam axis to irradiate the target supported by the target support, said radiation beam penetrating into the target,
wherein the radiation apparatus has a control system at least comprising a beam penetration depth control allowing at least to control and vary the penetration depth of the radiation beam into the target,
a radiation beam range sensor device adapted to determine the penetration depth of said radiation beam into the target, wherein said range sensor device comprises a gamma camera responsive to prompt gamma rays that are emitted while said radiation beam penetrates into the target, said gamma camera comprising:
- a collimator having a wall that blocks gamma radiation and an aperture in said wall,
- a detector comprising one or more scintillation elements upon which gamma radiation passing through said aperture of the collimator is incident,
- an electronic readout mechanism associated with said detector, wherein the collimator of the gamma camera is a slit collimator having an elongated slit aperture, wherein the detector comprises an array of multiple elongated scintillation elements in parallel and side-by-side arrangement, each scintillation element having a length along a longitudinal axis that is parallel to the collimator slit aperture, a width perpendicular to said length and parallel to an incident face of said scintillation element, and a height perpendicular to said length and perpendicular to an incident face of said scintillation element, wherein said length is greater than each of said width and said height.

15. A hadron radiation installation adapted to subject a target to irradiation by a hadron radiation beam, said installation comprising:
- a target support configured to support a target;
- a hadron radiation apparatus adapted to emit a hadron radiation beam along a beam axis to irradiate the target supported by the target support, said radiation beam penetrating into the target, wherein the radiation apparatus has a control system at least comprising a beam penetration depth control allowing at least to control and vary the penetration depth of the radiation beam into the target,

- a radiation beam range sensor device adapted to determine the penetration depth of said radiation beam into the target, wherein said range sensor device comprises a gamma camera responsive to prompt gamma rays that are emitted while said radiation beam penetrates into the target, said gamma camera comprising:
- a collimator having a wall that blocks gamma radiation and an aperture in said wall,
- a detector comprising one or more scintillation elements upon which gamma radiation passing through said aperture of the collimator is incident, and
- an electronic readout mechanism associated with said detector, wherein the collimator of the gamma camera is a slit collimator having an elongated slit aperture, wherein the detector comprises an array of multiple elongated scintillation elements in parallel and side-by-side arrangement, each scintillation element having a length along a longitudinal axis that is parallel to the collimator slit aperture, a width perpendicular to said length and parallel to an incident face of said scintillation element, and a height perpendicular to said length and perpendicular to an incident face of said scintillation element, and wherein the scintillation elements in a central group of scintillation elements (24) of said array each have a smaller width than the width of individual scintillation elements in end groups of scintillation elements between which end groups said central group is located.

16. The installation according to clause 15, wherein the gamma camera is movably supported so as to be movable in a Z-axis direction substantially parallel to the beam axis without moving the target support relative to said radiation apparatus and wherein a Z-axis drive is provided to controllable move the gamma camera in said Z-axis direction.

17. The installation according to clause 16, wherein the Z-axis drive is linked to the control system, and wherein said radiation session control data includes data representing one or more planned beam penetration depths of a radiation session to be performed, as well as data representing one or more planned collimator Z-axis positions for the Z-axis drive, e.g. said radiation session control data including data representing a pattern of Z-axis motion of the gamma camera in synchronicity with a planned pattern of varying beam penetration depth for the radiation session to be performed.

18. A hadron radiation installation adapted to subject a target to irradiation by a hadron radiation beam, said installation comprising:
- a target support configured to support a target;
- a hadron radiation apparatus adapted to emit a hadron radiation beam, preferably a pencil beam, along a beam axis to irradiate the target supported by the target support, said radiation beam penetrating into the target, wherein the radiation apparatus has a control system at least comprising a beam penetration depth control allowing at least to control and vary the penetration depth of the radiation beam into the target,

- a radiation beam range sensor device adapted to determine the penetration depth of said radiation beam into the target, wherein said range sensor device comprises a gamma camera responsive to prompt gamma rays that are emitted while said radiation beam penetrates into the target, said gamma camera comprising:
- a collimator having a wall that blocks gamma radiation and an aperture in said wall,
- a detector comprising one or more scintillation elements upon which gamma radiation passing through said aperture of the collimator is incident,
- an electronic readout mechanism associated with said detector, wherein the collimator of the gamma camera is a slit collimator having an elongated slit aperture, wherein the slit aperture having non-parallel faces defining an opening angle of the slit aperture and a corresponding field of view, and wherein the radiation beam range sensor device comprises one or more gamma cameras that provide multiple slit apertures at axially spaced positions relative to the beam axis, the axial spacing between successive slit apertures being at least 3 centimeters each slit aperture providing a field of view having an opening angle, which field of view is intersected by the pencil beam in operation of the installation, the fields of view provided by successive slit apertures adjoining one another so as to establish a continuous field of view along a section of the beam axis.

19. The installation according to clause 18, wherein all slit apertures are fixed width slit apertures.

20. The installation according to clause 18 or 19, wherein the radiation beam range sensor has 2 to 6 slit apertures.

21. The installation according to any of clauses 18-20, wherein the beam range sensor device comprises multiple gamma cameras, each gamma camera having a single slit aperture.

22. The installation according to any of clauses 18-21, wherein—when seen in a plane transversely to the beam axis—the slit apertures are arranged at different angular positions relative to the target support.

23. The installation according to any of clauses 18-22, wherein the installation comprises a gamma camera support device supporting multiple gamma cameras, said support device being adapted to allow for adjustment of one or more camera positions relative to the beam axis causing adjustment of the overlap of their fields of view.

24. The installation according to any of clauses 18-23, wherein the beam range sensor device comprises at least one gamma camera, preferably only has a single one gamma camera, that has multiple slit apertures at said axially spaced positions of claim 18.

25. A hadron radiation installation adapted to subject a target to irradiation by a hadron radiation beam, said installation comprising:
   a target support configured to support a target;
   a hadron radiation apparatus adapted to emit a hadron radiation beam, preferably a pencil beam, along a beam axis to irradiate the target supported by the target support, said radiation beam penetrating into the target,
   wherein the radiation apparatus has a control system at least comprising a beam penetration depth control allowing at least to control and vary the penetration depth of the radiation beam into the target,
      a radiation beam range sensor device adapted to determine the penetration depth of said radiation beam into the target, wherein said range sensor device comprises a gamma camera (20) responsive to prompt gamma rays that are emitted while said radiation beam penetrates into the target,
   said gamma camera comprising:
      a collimator having a wall that blocks gamma radiation and an aperture in said wall,
      a detector comprising one or more scintillation elements upon which gamma radiation passing through said aperture of the collimator is incident,
      an electronic readout mechanism associated with said detector,
   wherein the collimator of the gamma camera is a slit collimator having an elongated slit aperture,
   wherein the slit aperture having non-parallel faces defining an opening angle of the slit aperture and a corresponding field of view, and
   wherein the slit aperture is formed by two spaced apart collimator main wall portions, each defining an outer side face of the slit aperture, and an elongated collimator wall rod member of radiation blocking material, which rod member is arranged in between and spaced from said two spaced apart main wall portions to form a first and second slit passage of the slit aperture, said rod member defining inner side faces that each bound in combination with an adjacent outer side face one of said slit passages, the inner and outer side faces bounding each slit passage being non-parallel and defining an opening angle and corresponding field of view of the slit passage, each slit passage having a central plane of maximum transmission, the central planes of said first and second slit passage being non-parallel and intersecting one another so the fields of view of the slit passages overlap partly and in combination define a total field of view of the slit aperture.

26. The installation according to clause 25, wherein—when seen in the direction of the beam axis towards the detector of a gamma camera-the outer side faces of the slit aperture of the collimator have parallel outer side face portions at the side of the collimator remote from the detector and have diverging outer side face portions at the side facing the detector, and wherein the collimator wall rod member has diverging inner side face portions at the side of collimator remote from the detector and parallel inner side face at the side facing the detector.

27. The installation according to clauses 25 or 26, wherein the first and second slit passages are shaped to have equal opening angles.

28. The installation according to any of clauses 25-27, wherein the gamma camera is such that a gamma radiation image emanating from the field of view of a first slit passage does not overlap on the detector with a gamma radiation image emanating from the field of view of the second slit passage.

29. The installation according to clauses 25-28, wherein a blunt edge angle is present in an outer side face of each main wall part having an angle which is equal or greater than 150°.

30. The installation according to any of clauses 25-29, wherein multiple elongated collimator wall rod members are arranged in between said two spaced apart main wall portions and parallel to one another to form one or more central slit passages in addition to said first and second slit passages, each central slit passages being bounded by non-parallel faces of neighbouring wall rod members and defining an opening angle and corresponding field of view of the central slit passage, the fields of view of the slit passages overlapping partly and in combination defining the field of view of the slit aperture.

31. A method for hadron radiation therapy verification using a hadron radiation installation according to one or more of the preceding clauses wherein a target embodied as a phantom is subjected in a radiation session to irradiation by a hadron radiation beam, said method comprising:
   arranging the phantom on the target support;
   operating the hadron radiation apparatus to emit a hadron radiation beam along a beam axis to irradiate the phantom supported by the target support, said radiation beam penetrating into the phantom, and
   determining with the radiation beam range sensor device the actual penetration depth of said radiation beam into the phantom.

32. The method according to clause 31, wherein use is made of an installation wherein the control system is adapted to input and store in a memory one or more sets of radiation session control data corresponding to one or more radiation sessions to be performed with the radiation beam apparatus,
   and wherein the collimator is embodied at least according to claim 1 and has a slit width actuator mechanism that is linked to the control system,
   and wherein the verification radiation session is performed on the basis of stored radiation session control data including data representing a pattern of varying beam penetration depth during the session,
   and wherein the verification radiation session is performed on the basis of stored radiation session control data including data representing a pattern of variation of the slit width of the collimator to be performed in synchronicity with the varying beam penetration depth pattern.

33. The method according to clauses 31 or 32, wherein use is made of an installation according to claim 10, wherein the verification radiation session is performed on the basis of stored radiation session control data including data representing a pattern of varying beam penetration depth during the session, and wherein the verification radiation session is performed on the basis of stored radiation session control data including data representing a pattern of Z-axis motion of the collimator in synchronicity with the planned pattern of varying beam penetration depth for the radiation session to be performed, preferably so as to allow the Bragg peak of the emitted radiation beam to be located in a central plane of the collimator which is a plane of geometrical symmetry through the slit aperture of the collimator.

34. A method for determination of penetration depth of a hadron beam into a target, wherein use is made of a radiation beam range sensor device as described in one or more of the preceding clauses.

35. A method for imaging a hadron beam penetrating into a target irradiated by a hadron radiation beam, wherein use is made of a radiation beam range sensor device as described in one or more of the preceding clauses.

The invention claimed is:

1. A method for performing a proton radiation therapy verification session using a proton radiation installation comprising:
   a target support configured to support a target;
   a proton radiation apparatus adapted to emit a proton radiation beam along a beam axis to irradiate the target supported by the target support, said radiation beam penetrating into the target,
   wherein the radiation apparatus has a control system at least comprising a beam penetration depth control allowing at least to control and vary the penetration depth of the radiation beam into the target,
   a radiation beam range sensor device adapted to determine the penetration depth of said radiation beam into the target, wherein said range sensor device comprises a gamma camera responsive to prompt gamma rays that are emitted while said radiation beam penetrates into the target,
   said gamma camera comprising:
      a collimator having a wall that blocks gamma radiation and an aperture in said wall,
      a detector comprising one or more scintillation elements upon which gamma radiation passing through said aperture of the collimator is incident, and
      an electronic readout mechanism associated with said detector,
   wherein the collimator of the gamma camera is a slit collimator having an elongated slit aperture,
   wherein the gamma camera is movably supported so as to be movable in a Z-axis direction substantially parallel to the beam axis without moving the target support relative to said proton radiation apparatus,
   a Z-axis drive adapted to controllable move the gamma camera in said Z-axis direction, wherein the Z-axis drive is linked to the control system,
   wherein the control system is adapted to input and store in a memory of the control system one or more sets of radiation session control data corresponding to one or more radiation sessions to be performed with the proton radiation apparatus,
   wherein the method for performing said proton radiation therapy verification session comprises:
   arranging a phantom on the target support,
   storing in the memory data representing a pattern of varying beam penetration depth during the proton radiation therapy verification session,
   storing in the memory data representing a pattern of Z-axis motion of the collimator in synchronicity with the pattern of varying beam penetration depth during the proton radiation therapy verification session,
   operating the proton radiation apparatus and emitting a proton radiation beam along the beam axis to irradiate the phantom supported by the target support, said radiation beam penetrating into the phantom with said varying beam penetration depth, and
   operating the Z-axis drive to move the collimator in synchronicity with the pattern of varying beam penetration depth without moving the target support relative to said proton radiation apparatus.

2. A method for performing a proton radiation therapy verification session using a proton radiation installation comprising:
   a target support configured to support a target;
   a proton radiation apparatus adapted to emit a proton radiation beam along a beam axis to irradiate the target supported by the target support, said radiation beam penetrating into the target,
   wherein the radiation apparatus has a control system at least comprising a beam penetration depth control allowing at least to control and vary the penetration depth of the radiation beam into the target,
   a radiation beam range sensor device adapted to determine the penetration depth of said radiation beam into the target, wherein said range sensor device comprises a gamma camera responsive to prompt gamma rays that are emitted while said radiation beam penetrates into the target,
   said gamma camera comprising:
   a collimator having a wall that blocks gamma radiation and an aperture in said wall,
   a detector comprising one or more scintillation elements upon which gamma radiation passing through said aperture of the collimator is incident, and
   an electronic readout mechanism associated with said detector,
   wherein the collimator of the gamma camera is a slit collimator having an elongated slit aperture,
   wherein the collimator is a variable width slit collimator having an elongated slit aperture of variable width, said collimator comprising a first collimator member and a second collimator member that each define one of the opposed longitudinal edges of the slit aperture, said collimator having a slit width actuator mechanism for displacing and positioning said first and second collimator members relative to one another,
   wherein the slit width actuator mechanism is linked to the control system,
   wherein the method for performing the proton radiation therapy verification session comprises:
   arranging a phantom on the target support,
   operating the proton radiation apparatus to emit a proton radiation beam along the beam axis to irradiate the phantom supported by the target support, said radiation beam penetrating into the phantom, and
   determining with the radiation beam range sensor device an actual penetration depth of said radiation beam into the phantom;
   wherein the control system is adapted to input and store in a memory thereof one or more sets of radiation session control data corresponding to one or more radiation sessions to be performed with the proton radiation apparatus, wherein the method for performing the proton radiation therapy verification session comprises:

arranging a phantom on the target support, storing in the memory data representing a pattern of varying beam penetration depth during the proton radiation therapy verification session, storing in the memory data representing a pattern of variation of the slit width of the collimator to be performed by the slit width actuator mechanism in synchronicity with the varying beam penetration depth pattern during the proton radiation therapy verification session, operating the proton radiation apparatus and emitting a proton radiation beam along the beam axis to irradiate the phantom supported by the target support, said radiation beam penetrating into the phantom with said varying beam penetration depth, and operating the slit width actuator mechanism in synchronicity with the varying beam penetration depth pattern during the proton radiation therapy verification session.

3. The method according to claim 2, wherein the electronic readout mechanism associated with said detector provides real-time feedback to the control system.

4. The method according to claim 2, wherein the gamma camera is movably supported so as to be movable in a Z-axis direction substantially parallel to the beam axis without moving the target support relative to said proton radiation apparatus, and wherein a Z-axis drive is provided to controllable move the gamma camera in said Z-axis direction, and wherein the Z-axis drive is linked to the control system, wherein the control system is adapted to input and store in a memory of the control system one or more sets of radiation session control data corresponding to one or more radiation sessions to be performed with the proton radiation apparatus, wherein the method for performing said proton radiation therapy verification session further comprises:

storing in the memory data representing a pattern of Z-axis motion of the collimator in synchronicity with the pattern of varying beam penetration depth during the proton radiation therapy verification session, and operating the Z-axis drive to move the collimator in synchronicity with the pattern of varying beam penetration depth without moving the target support relative to said proton radiation apparatus.

* * * * *